United States Patent [19]

Kawano et al.

[11] Patent Number: 4,790,567
[45] Date of Patent: Dec. 13, 1988

[54] CONNECTOR FOR PLASMAPHERESIS BAG

[75] Inventors: Yukihiro Kawano, Yokohama; Tomishiro Juji, Tokyo; Toshihiko Ono, Oita; Hirofumi Iga, Oita; Seiichi Ono, Oita; Yoshiyuki Isobe, Oita, all of Japan

[73] Assignee: Kawasumi Laboratories, Inc., Tokyo, Japan

[21] Appl. No.: 136,860

[22] Filed: Dec. 22, 1987

Related U.S. Application Data

[63] Continuation of Ser. No. 893,898, Jul. 29, 1986, abandoned.

[30] Foreign Application Priority Data

| Jul. 31, 1985 | [JP] | Japan | 60-167650 |
| Oct. 23, 1985 | [JP] | Japan | 60-161328 |
| Oct. 30, 1985 | [JP] | Japan | 60-241376 |
| May 9, 1986 | [JP] | Japan | 61-68838 |

[51] Int. Cl.⁴ .................................... F16L 35/00
[52] U.S. Cl. ............................ 285/24; 285/319; 285/330; 285/331; 285/914; 285/915; 285/921; 285/93; 604/6; 128/771
[58] Field of Search ............... 285/330, 914, 12, 319, 285/320, 24, 331, 915, 921, 93; 128/204.18, 200.21, 771, 912; 604/7, 48, 6, 905, 175, 248, 110

[56] References Cited

U.S. PATENT DOCUMENTS

| 2,997,681 | 8/1961 | Klassen | 439/268 |
| 3,144,292 | 1/1961 | Forney et al. | 439/16 |
| 3,194,588 | 7/1965 | Buckey et al. | 285/914 |
| 3,287,031 | 11/1966 | Simmons et al. | 285/914 |
| 3,523,522 | 8/1970 | Whitehead | 128/771 |
| 3,625,212 | 12/1971 | Rosenberg | 604/6 |
| 4,057,080 | 11/1977 | Baber et al. | 285/914 |
| 4,195,631 | 4/1980 | Baucom | 604/6 |
| 4,219,021 | 8/1980 | Fink | 604/248 |
| 4,280,723 | 7/1981 | Moldestad | 285/914 |
| 4,407,660 | 10/1983 | Nevens et al. | 604/6 |
| 4,433,973 | 2/1984 | Kurtz et al. | 604/905 |
| 4,617,640 | 10/1986 | Potolsky et al. | 285/914 |
| 4,655,741 | 4/1987 | Kamishima | 604/6 |

FOREIGN PATENT DOCUMENTS

| 670440 | 9/1963 | Canada | 285/914 |
| 816582 | 7/1969 | Canada | 285/914 |
| 1187435 | 2/1965 | Fed. Rep. of Germany | 285/914 |
| 2141249 | 3/1972 | Fed. Rep. of Germany | 285/914 |
| 771968 | 4/1957 | United Kingdom | 285/914 |

Primary Examiner—Dave W. Arola
Attorney, Agent, or Firm—Michael J. Striker

[57] ABSTRACT

The present invention is a connector to be provided on way of a blood restoring circuit of a plasmapheresis bag set, comprising a male connecting member and a female connecting member.

Each of the members is provided with a key ring of a structure in laminated layer, and the key rings are formed, at ends with a convex or a groove for having combination of the both members.

The connecting members are provided with positioning means therefor, and positionings of the convex or the groove of the key rings are adjusted per each of the connectors.

14 Claims, 6 Drawing Sheets

FIG_8

FIG_9

FIG_10

FIG_11

FIG_12

FIG_13

FIG_14
(PRIOR ART)

FIG_15
(PRIOR ART)

CONNECTOR FOR PLASMAPHERESIS BAG

This is a continuation, of application Ser. No. 893,898, filed July 29, 1986 now abandoned.

BACKGROUND OF THE INVENTION

1. Field of the Invention

The present invention relates to a connector for plasmapheresis bag set which is used for exsanguinating or drawing the blood from a blood donor, dividing a blood component and a blood plasma component, and after having stored the blood plasma component only, restoring a rest blood component to the blood donor.

2. Description the Prior Art

FIG. 25 shows an outlined view of a conventional plasmapheresis bag.

A plasmapheresis bag 400 comprises a pair of a blood exsanguinating bag 401 and a blood plasma dividing bag 402, and, if required, comprises a combination of two or three pairs.

The bag 401 is connected at its top to a blood drawing tube 403 which communicates with a blood restoring tube 405 having an exit 404 and a branched blood exsanguinating tube 407 having a needle 406.

Said bag 401 is furnished with a blood transfusing mouth 408 and a protector 409 therefor, and is connected to a tube 410 communicating with the blood plasma dividing bag 402 via a communication piece 410a.

In the prior art, when the above mentioned plasmapheresis bag 400 was composed of only a pair of the blood bag 401 and the blood plasma separating bag 402, it has been used as mentioned below.

The blood drawing needle 406 is pierced into a blood tube of the blood donor, and the blood is introduced into the blood bag 401 via the tubes 407 and 403. When a determined amount of the blood is gathered, the needle 406 is covered with the cap 411, and the tube 403 is closed by welding and cut off. The bag 401 supporting the blood and the blood plasma separating bag 402 connected to the blood bag 401 are subjected to a centrifugal machine for dividing the blood in the bag 401 into the blood component and the blood plasma component.

Subsequently, the communication piece 410a is broken to open a flowing path, and a supernatant blood plasma component only is guided to the blood separating bag 402 via the communicating tube 410, while the blood component remaining in the bag 401 is restored to the blood donor through a blood transfusion set 420 as shown in FIG. 26.

The blood transfusion set 420 is composed of a bottle 421 supporting a physiological saline solution containing an anti-coagulation agent, an introduction tube 422, a blood restoring needle 424, an instillation tube 425, a blood restoring tube 426, a clamp 427, and an adapter 428 provided at an end of said tube 426 and fittable to said exit 404.

For use, the saline solution is in advance filled in the blood restoring tube 426 of the blood transfusion set 420, the saline solution introducing tube 422 and the instillation tube 425. The adapter 428 is connected to the blood returning exit 404 and the needle 406 is again pierced into the blood tube of the blood donor, and a blood restoring needle 424 is passed through the blood transfusion mouth 408 of the bag 401. Subsequently, the blood component in the bag 401 is introduced to the instillation tube 425 via the tube 429, and is diluted by the saline solution in the instillation tube 425 and restored to the blood donor via the tubes 426, 405 and 407.

When the plasmapheresis bag set 400 is used, it must be confirmed that the blood component to be restored to the blood donor is the same type.

Confirmation has been carried out in the conventionally as follows.

(1) Checking the blood donor's name and the name of the label of the blood exsanguination bag 401, (2) Checking the number given to the blood donor and the number of the label of the blood bag 401, (3) Checking the blood donor and the label attached to the blood bag 401.

However, since nowadays the blood plasma producing agents are much required and the blood donors of several hundreds is dealed with a day, human careless mistakes of confusing the names or numbers, or attaching places of the labels might be caused during working to invite vital troubles of the blood transfusion.

SUMMARY OF THE INVENTION

In a blood exsanguination bag is separated from the plasmapheresis bag set and undergoes a centrifugal separation process, and the blood plasma component is obtained. Afterward, said bag is once again connected to said set, and for such a case that the blood component is returned to the blood donor, the present invention is to provide a connector which may exactly connect the separated exsanguinating bag to the initial plasmapheresis bag set, so that erroneous accidents between the blood donor and the blood component to be restored are avoided without fail.

A second object of the invention is to provide a connector which can be easily connected without requiring special technique, and keep blood running paths hygienical.

A third object of the invention is to provide a compact connector which is easily set up and is produced at low cost.

The above mentioned object of the invention will be accomplished by an under mentioned connector for the plasmapheresis bag.

The connector of the invention comprises a male connecting member and a female connecting member, and these connecting members are provided with key rings respectively, and the key rings are defined, at ends thereof, with engaging portions when said both members are connected, and are provided with positioning means.

DESCRIPTION OF PREFERRED EMBODIMENTS

The present invention will be explained with reference to embodiments shown in the attached drawings.

Figure 1:
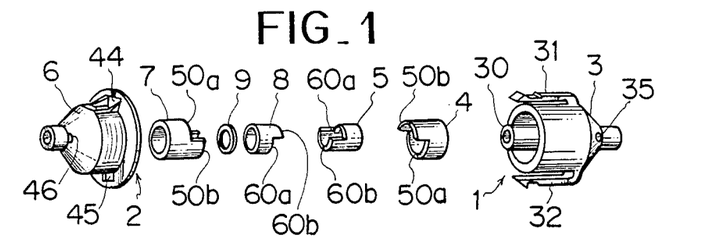
FIG. 1 is a perspective view of a disassmbled connector according to the invention.
Figure 2:
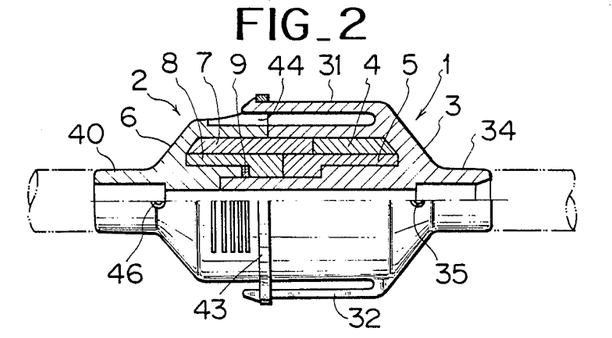
FIG. 2 is a front view showing an upper half part of the connector in cross section.

FIG. 1 is a perspective view of a disassembled connector and FIG. 2 is a front view showing an upper half part of the connector in cross section.

In the same, the numeral 1 is a male member and 2 is a female member. The male member 1 is composed of a housing 3, a key ring 4 of large diameter and a key ring 5 of small diameter. The female member 2 is also composed of a housing 6, a key ring 7 of large diameter and a key ring 8 of small diameter. Either one of the small diametered key rings 5, 8 is inserted with a seal packing 9.

Figures 3A, 3B, 3C:
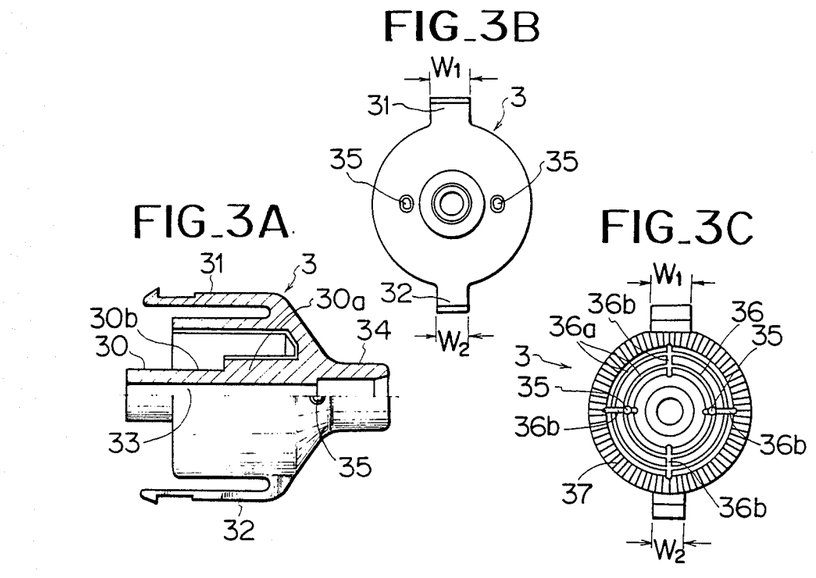
FIG. 3A is a front view showing an upper half part of a housing of a male member in cross section.
FIG. 3B is a right side view of the housing of the male member.
FIG. 3C is a left side view of the housing of the male member.

FIGS. 3A, B and C show in detail the housing 3 of the male member 1 which is shaped in cup as a whole and projected at a rear part, with a tube connecting mouth 34 and formed centrally with a blood path 33 as well as a male connecting tube 30 at a center of an inner part.

The male connecting tube 30 is formed, at an outer side, with a step of a large diametered part 30a at a rear part and a small diametered part 30b at a front part.

The housing 3 is formed with a pair of hooks 31, 32 at an upper and a lower part, having elasticity in vertical directions, and the hook 31 has a width W1 larger than a width W2 of the other hook 32.

In such a manner, a vertically reversed connection of the male and female members is never made, and since the hooks are provided at the two parts, the connection is secured. If thicknesses are made different in the hooks 31 and 32, said reversed connection may be avoided.

The housing 3 is formed, at its rear part, with a plurality of bonding agent pouring holes 35, 35 passing to the interior of the housing, and is formed, at its inner wall, with a bonding agent guide groove 36 which is, as seen in FIG. 3C, composed of a plurality of circular grooves 36a formed at an inner wall and a plurality of grooves 36b communicating with said circular grooves 36a and extending in length of an inner wall of the housing and in length of said large diametered part 30a.

The housing is marked with scalings 37 at the end of the opening, which are each marked per, e.g. 5° circumferentially around a core of the housing.

Figures 4A, 4B:
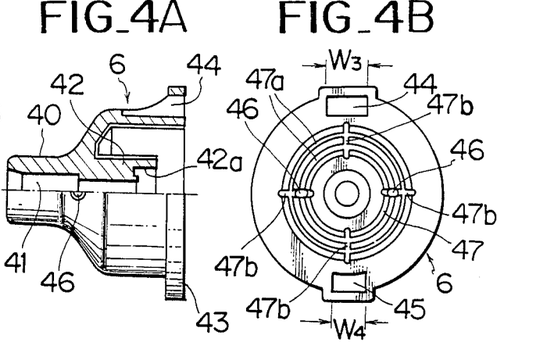
FIG. 4A is a front view showing an upper half part of a housing of a female member in cross section.
FIG. 4B is a right side view of the housing of the female member.
Figure 4C:
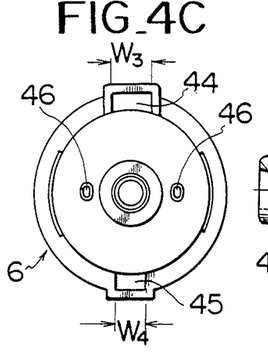
FIG. 4C is a left side view of the housing of the female member.

FIGS. 4A, B, C show in detail a housing 6 of the female member 2 which is shaped in cup as a whole and projected at a rear part with a tube connecting mouth 40 and formed centrally with a blood path 41 as well as a female connecting tube 42 at a center of an inner part.

The female connection tube 42 is formed with a concave 42a at its end to which the end portion of the male connection tube 30 has access.

The housing 6 is formed with a flange 43 on the outer circumference in the opening side, which is opend with engaging holes 44, 45 corresponding to the hooks 31, 32 of the housing 3 of the male member as shown in FIGS. 4B and 4C, and the hole 44 has a larger width W3 than W4 of the hole 45.

The housing 6 is formed similarly as mentioned above, at its rear part, with a plurality of bonding agent pouring holes 46, 46 passing to the interior of the housing, and is formed, at its inner wall, with a bonding agent guide groove 47 which communicates with said holes 46, 46, and is also composed of a circular groove 47a and a plurality of grooves 47b extending in length of an inner circumferential wall of the housing and in length of an outer face of said communication tube 42.

Figure 5A:
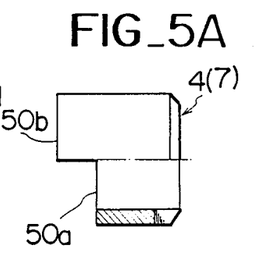
FIG. 5A is a front view of a lower half part of a key ring of large diameter in cross section.
Figure 5B:
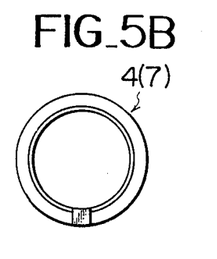
FIG. 5B is a right side view of the large diametered key ring.
Figure 5C:
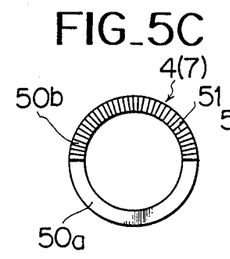
FIG. 5C is a left side view of the large diametered key ring.

FIGS. 5A, B, C show in detail the large diametered key rings 4, 7 which are formed with a concave 50a and a convex 50b by cutting out a half part of a circumference at an end of the tube body, and the convex 50b is marked with scalings 51 which are each marked per, e.g. 5° circumferentially around a core of the housing, as similarly the scaling 37 of the housing 3 of the male member.

Figure 6A:
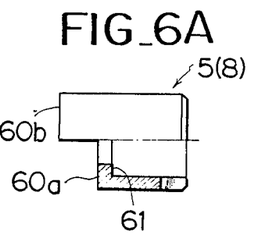
FIG. 6A is a front view showing a lower half part of a key ring of small diameter in cross section.
Figure 6B:
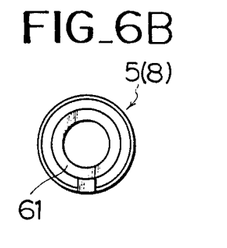
FIG. 6B is a right side view of the small diametered key ring.
Figure 6C:
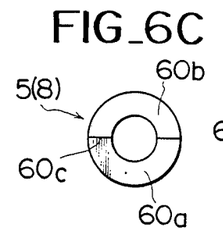
FIG. 6C is a left side view of the small diameterd key ring.

FIGS. 6A, B, C shows in detail the small diametered key rings 5, 8 which are formed with a concave 60a and a convex 60b by cutting out a half part of a circumference at an end of the tube body, and the convex 60a is formed with a project ed flange 61. The small diametered key ring 8 is to be incorporated in the housing of the female member, and is inserted with a seal packing material 9 as shown in FIG. 1 so as to contact to said flange 61.

A further explanation will be made to one example of setting-up of the above mentioned connector.

Figure 7:
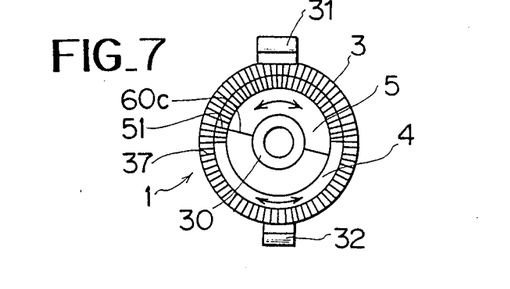
FIG. 7 is a left side view of the male member.

At first, as shown in FIG. 7, the housing 3 of the male member 1 is inserted with the large diametered key ring 4 and the small diametered key ring 5, and a convex cutout 60c of the small diametered key ring 5 is met to one of the scalings 51 of the large diametered key ring 4, and one of the scalings 51 of the large diametered key ring 4 is met to one of the scalings 37 of the housing 3. If the scale is slided one by one, combinations of 72×72×72=373248 (the scalings are marked per 5°) are obtained in total.

The key rings 4, 5 are adjusted in positioning of the angular rotation, and the bonding agent is poured into the hole 35. The bonding agent flows from the guide groove 36 into between the outer circumference of the large diametered key ring 4 and the inner circumference of the housing 3, and between the inner circumference of the small diametered key ring 5 and the outer circumference of the large diametered part 30a of the male connecting tube 30. It becomes hardened as flowing so that the key rings 4, 5 are secured to the housing.

On the other hand, the female member 2 is also inserted, in the housing 6, with the large diametered key ring 7 and the small diametered key ring 8, and the rotational angle is adjusted such that the key rings 7, 8 are fitted with the key rings 4, 5 with respect to the concave and convex, and the bonding agent is poured into the holes 46, 46 of the housing 6 so as to secure the key rings 4, 5 to the housing 6 similarly as the male member 1. When the small diametered key rings 5, 8 and the large diameterd key rings 4. 7 are met a tube has a double layer.

In the above embodiment, the connector comprises the large diametered key ring and the small diametered key ring, but if kinds of the combination may be reduced, either one will be omitted, and if many kinds are required other key rings will be added.

The bonding agent guiding grooves 36, 37 are not limited to the shown ones, but any types will be enough if the key rings are exactly secured.

For materials of the housings or key rings, synthetic resins excellent in suiting to human living bodies are preferable, for example, polycarbonate, polypropelen, vinyl chloride or the like are used. For the seal packing material rubber or elastic synthetic resin are used.

Figure 8:
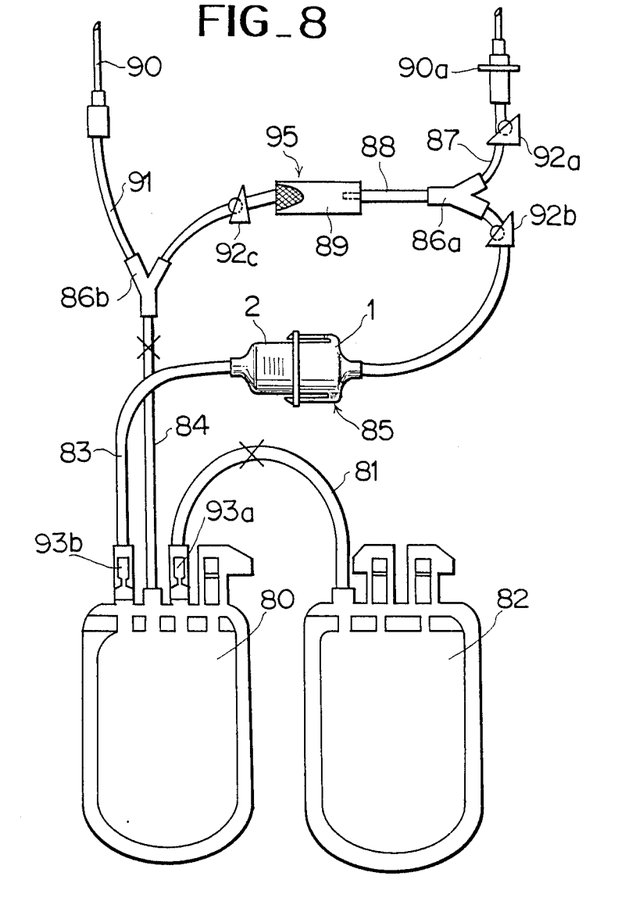
FIG. 8 a whole view of a plasmapheresis bag set provided with a connector of the invention.

FIG. 8 shows an embodiment where the connector of the invention is applied to a plasmapheresis bag system.

A blood tranfusion bag 80 is connected to a blood plasma separating bag 82 via a connection tube 81, and to a blood restoring tube 83 and a blood guiding tube 84. The blood restoring tube 83 is, on half way, connected to the connector 85 of the present invention, and a tube extending therefrom is connected to a Y-tube 86a which is connected to a tube 87 having a physiological saline solution guide needle 90a and to a tube 88 for mixing the blood and the physiological saline solution.

The mixing tube 88 is provided with an instillation tube 89, and a tube extending therefrom is connected to a Y-tube 86b which is connected to a tube 91 having a blood guiding needle 90 and said blood guiding tube 84.

In the same, numerals 92a, 92b, 92c designate flowing amount adjusting clamps, and the numerals 93a, 93b designate communication pieces.

The above plasmapheresis bag will be referred to in its usage.

When the blood drawing bag 80 is positioned above a blood doner and the needle 90 is pierced into his blood tube, the blood is guided to a blood bag 37 via the tubes 91, 84. Then, the clamps 92a, 92b, 92c are closed.

After a determined amount of the blood is guided, the tube 84 is closed with a welder and cut off, the connector 85 is divided into the male part 1 and the female part 2, and they are shielded with caps for preventing from the air.

If the bag 80 supporting the blood is subjected to a centrifugal separation together with a blood plasma separation bag 82, the blood therein is divided into the blood component and the blood plasma component.

Subsequently, the communication piece 93a is cut off to transfer a supernatant blood plasma component in the blood bag 80 to said bag 82 via the communication tube 81.

The communication tube 91 is closed with the welder, and the blood bag 80 and the blood plasma bag 81 are cut off. The blood component only remains in the blood bag 80, and this blood component is returned to the blood donor.

The needle 90a is pierces into a container (not shown) enveloping the physiological saline solution, and the clamp 92a is released opened so as to guide the saline solution in the blood returning circuit 95 for performing a priming therein, after which, the needle 90 is again pierced into his blood tube, and the female member 2 of the connector 85 provided at the blood returning tube 83 of the blood bag 80 is connected to the male member 1. Said circuit 95 is composed of the male member 1, the needle 89, the tube 87, the mixing tube 88, the instillation bag 89, the blood needle 90, and the tube 91. The key rings 4, 5 of the member 1 and key rings The key rings 4, 5 of the male member 1 and the key rings 7, 8 of the female member 2 are arranged in proper positions per each of lots so that they are connected each other. Since the housings 3, 6 are so controlled that hooks 31, 32 are engaged with the engaging holes 43, 44 and in case of the blood bag 80 of the blood donor, the male member 1 and the female member 2 agree to each other, otherwise the both are not met.

Therefore, by the agreement of the both members 1 and 2, an identification of the blood donor and the blood component may be checked.

If the communication piece 93b and the clamps 92b, 92c are opened after communication of the male member 1 and the female member 2, the blood component in the bag is guided to the blood returing circuit 95, and it is completely mixed with the saline solution and diluted, and returned to the blood donor The connector of the invention may be, of course, applied to (a) plasmapheresis bag provided with more than two pairs of a blood bag—a blood plasma bag, and (b) plasmapheresis bag provided with more than one pair of a blood bag—a blood plasma separating bag—a small bag, other than the plasmapheresis bag as shown in FIG. 8.

Figure 9:
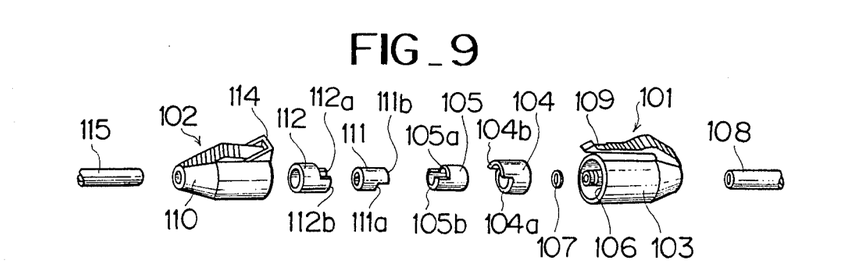
FIG. 9 is a perspective view of a disassembled connector of another embodiment of the invention.
Figure 10:
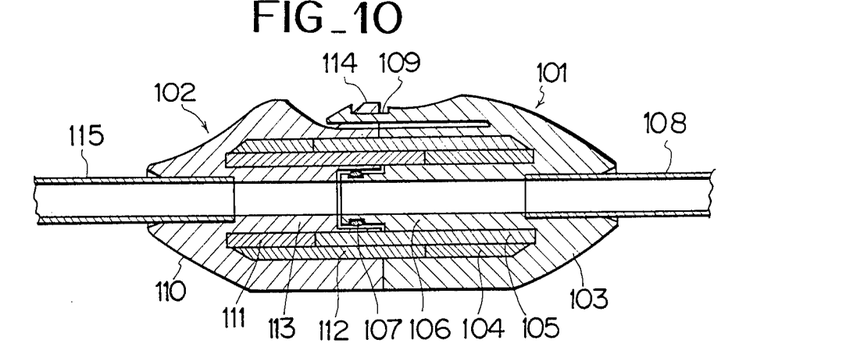
FIG. 10 is a vertically cross sectional view of a set-up connector of FIG. 9.

FIGS. 9 and 10 show another embodiment of the invention, and the numeral 101 is a male member and 102 is a female member.

The male member 101 comprises a housing 103 and a pair of large and small key rings 104, 105. The housing 103 is formed at its center with a connecting tube 106 to which a seal ring 107 is mounted. The housing 103 is provided, on an outside, with a hook 109 having elasticity in vertical directions, and connected, at a rear part, to a fluid tube 108.

The large diametered key ring 104 is fixedly inserted with the small diametered key ring 105 therewithin. The key rings 104, 105 are formed with concaves 104a, 105a and convexs 104b, 105b by cutting out the half part of its end part. The small diametered key ring 105 is inserted into the large diametered key ring 104 by sliding the concave and convex in the circumferential direction per each of the products.

The female member 102 also comprises a housing 110 and a pair of large and small key rings 111, 112 similarly to the male member.

The housing 110 is formed centrally with a communicating tube 113 into which an end portion of the communicating tube 116 of the male member, and is formed outsides with an engaging part 114 at a position corresponding to a hook 109 of the housing 101 of the male side, and further connected at a rear side with a fluid tube 115 communicating with the connecting tube 113.

The large diametered key ring 112 is inserted with the small diametered key ring 111 therein, and those are fixedly secured within the connecting tube 113. The key rings 111, 112 are formed with concaves 111a, 112a and convexes 111b, 112b and those correspond to concaves and convexes of the male key rings 104, 105 and are slided in a circumferential direction. The convexes 104b, 105b of the male key rings 104, 105 are engaged with the concaves 111a, 112a of the female key rings 111, 112.

Figure 11:
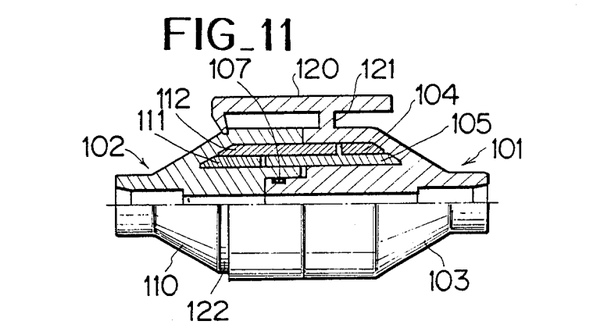
FIG. 11 is a front view of an upper half cross section showing another embodiment of a connecting means for male and female members.
Figure 12:
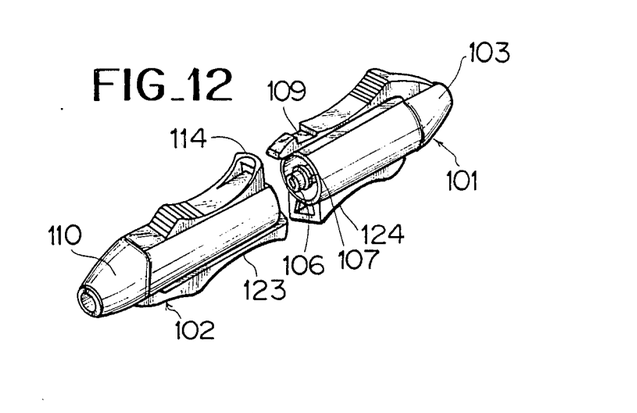
FIG. 12 is a perspective view showing a further engaging means of said two members.

FIG. 11 shows a modified example of an engaging part of the housing. The engaging part is provided with a hook 120 around a fulcrum of a supporter 121, said hook 120 being elastically movable in vertical directions, and being engaged, at its end portion, with a ring shaped groove 122 of the housing 110 of the female side. The hook 120 may be formed at the upper and lower sides.

FIG. 17 shows another embodiment of an engaging part of the housing. In addition to the hook 106 and the stopper 114 shown in FIGS. 9 and 10, a hook portion 123 and an engaging portion 124 are provided on the lower part of the housing in opposition facing directions. Since the key rings shown in the above embodiments have the same shapes of the male and female sides, mass-production is possible at low cost.

Figure 13:
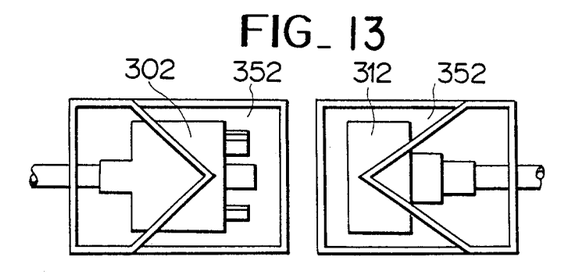
FIG. 13 is an outlined view of sealing the both members with a protector.
Figure 14:
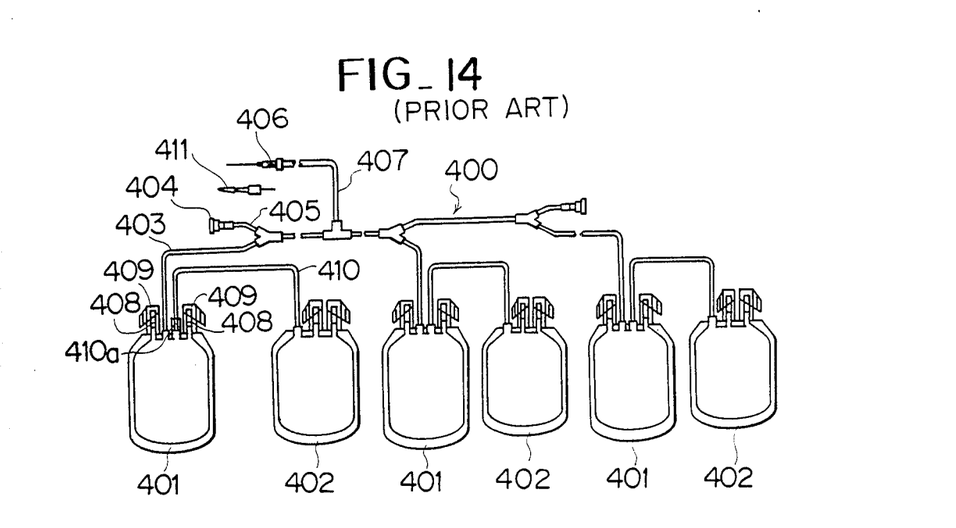
FIG. 14 is an outlined view of a foregoing plasmapheresis bag set.
Figure 15:
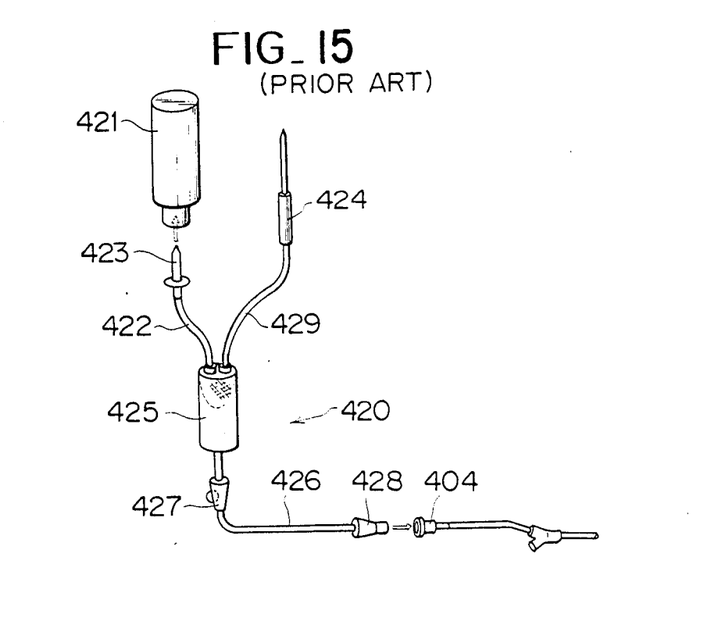
FIG. 15 is an outlined view of a blood restoring set to be connected to a foregoing plasmapheresis bag set.

The male member 302 and the female member 312 are in advance connected as shown in FIG. 8, and they are separated for use. As shown in FIG. 13, both members are separated and are housed air-tightly in a protector of soft plastic, which will be broken when the members are used.

In such a manner, it is no longer necessary to cap the bag against the air, after the blood of a determined amount is colleted in the blood bag, and the working is very hygienic.

The connector 85 shown in FIG. 8 is in advance divided into the male and female ones, and they may be maintained air-tight.

Each of the above mentioned embodiments is listed for example, and actual structure may be modified within claimed range. For instance, the composing elements of the male member are furnished to the female member, and the corresponding composing elements of the female member are furnished to the male member.

What is claimed is:

1. A plasmapheresis connector to be furnished on a tube path for restoring a blood component to a blood donor from a blood plasmapheresis bag set after a blood plasma component has been extracted from blood collected in a blood bag of the plasmapheresis bag set, the connector comprising:

a male connecting member and a female connecting member, each of said connecting members having a plurality of coaxially arranged rings of different diameters which radially overlap each other, said rings of said male connecting member corresponding diametrically with said rings of said female connecting member;

means for fixing said rings of said male connecting member against rotation relative to each other and to said male connecting member;

means for fixing said rings of said female connecting member against rotation relative to each other and to said female connecting member;

means for releasably keeping both of said connecting members together; said releasably keeping means including hook connecting means formed on at least one of said connecting members and receiving means formed on the other of said connecting members, said receiving means being formed to receive and releasably retain said hook connecting means so as to releasably keep said connecting members together;

means for making said male and female connecting members compatible only with each other to avoid mismatch; said making means including a projection extending longitudinally from each of said rings of both of said connecting members so that when said connecting members are brought together along a common axis, said projections on each of said rings of said male connecting member overlaps and locks against a respective one of said projections on said rings of said female connecting member so as to prevent said connecting members from being rotatable relative to each other; and means for providing a flow path through said connecting members to accommodate a flow of the blood to be restored.

2. A connector as defined in claim 1, wherein said connecting members have a housing with a positioning means for positioning said connecting members for alignment with each other.

3. A connector as defined in claim 1, wherein each of said members has a plurality of two of said rings spaced radially apart from each other and being radially inside of said releasably keeping means, said projections being formed and arranged relative to each other and to said releasably keeping means so as to have at most one relative angular position in which said connecting members are releasably kept together out of a total of 72×72×72 different possible combinations of said relative angular positions.

4. A connector as defined in claim 1, wherein said releasably keeping means includes a plurality of two hook connecting means and two receiving means formed on said connecting members, said two hook connecting means being formed with different widths, said two receiving means being formed with corresponding widths so that said two hook connecting means is fittable on said two receiving means.

5. A plasmapheresis connector to be furnished on a tube path for restoring a blood component to a blood donor from a blood plasmapheresis bag set after a blood plasma component has been extracted from blood collected in a blood bag of the plasmapheresis bag set, the connector comprising:

a male connecting member and a female connecting member, each of said connecting members having a plurality of coaxially arranged rings of different diameters which radially overlap each other, said rings of said male connecting member corresponding diametrically with said rings of said female connecting member;

means for providing a flow path for the blood component to be restored, said providing means including two elongated communication tubes each extending longitudinally from each of said connecting members respectively, one of said two elongated communication tubes being formed and arranged to be insertable and fittable into the other of said two elongated communication tubes when said connecting members are brought together;

means for releasably keeping both of said connecting members together; said releasably keeping means including hook connecting means formed on at least one of said connecting members and receiving means formed on the other of said connecting members, said receiving means being formed to receive and releasably retain said hook connecting means so as to releasably keep said connecting members together;

means for making said male and female connecting members compatible only with each other to avoid mismatch, said making means including a plurality of projections extending from said rings of both of said connecting members, each of said projections on said male connecting member being formed to overlap and lock against a respective one of said projections on said female connecting member so as to constitute compatible pairs of said projections and to prevent said connecting members from being rotatable relative to each other when said connecting members are brought together along a common axis and all of said compatible pairs of projections lock against each other simultaneously;

means for fixing said rings of one of said connecting members against rotation relative to said one connecting member and to each other after being rotated relative to each other into a distinct relative angular position; and means for fixing said rings of the other of said connecting members against rotation relative to said other connecting member and to each other after being rotated relative to each other into a relative angular position corresponding to said distinct angular position.

6. A connector as defined in claim 5, wherein said connecting members have a housing with a positioning means for positioning said connecting members for alignment with each other.

7. A connector as defined in claim 5; and further comprising:

means for sealing said flow path and including a sealing ring mounted on one of said two elongated communication tubes.

8. A connector as defined in claim 5, wherein each of said members has a plurality of two of said rings spaced radially apart from each other and being radially inside of said releasably keeping means, said projections being formed and arranged relative to each other and to said releasably keeping means so as to have at most one relative angular position in which said connecting members are releasably kept together out of a total of 72×72×72 different possible combinations of said relative angular positions.

9. A connector as defined in claim 5, wherein said releasably keeping means includes a plurality of two hook connecting means and two receiving means formed on said connecting members, said two hook connecting means being formed with different widths, said two receiving means being formed with corresponding widths so that said two hook connecting means is fittable on said two receiving means.

10. A plasmapheresis connector to be furnished on a tube path for restoring a blood component to a blood donor from a blood plasmapheresis bag set after a blood plasma component has been extracted from blood collected in a blood bag of the plasmapheresis bag set, the connector comprising:

a male connecting member and a female connecting member, each of said connecting members having a plurality of coaxially arranged rings of different diameters which radially overlap each other, said rings of said male connecting member corresponding diametrically with said rings of said female connecting member;

means for providing a flow path for the blood component to be restored, said providing means including two elongated communication tubes each extending longitudinally from each of said connecting members respectively, one of said two elongated communication tubes being formed and arranged to be insertable and fittable into the other of said two elongated communication tubes when said connecting members are brought together;

means for releasably keeping both of said connecting members together; said releasably keeping means including hook connecting means formed on at least one of said connecting members and receiving means formed on the other of said connecting members, said receiving means being formed to receive and releasably retain said hook connecting means so as to releasably keep said connecting members together;

means for making said male and female connecting members compatible only with each other to avoid mismatch; said making means including a projection extending from each of said rings of both of said connecting members, each of said projections on said male connecting member being formed to overlap and lock against a respective one of said projections of said female connecting member when said connecting members are brought together along a common axis;

means for fixing said rings of one of said connecting members against rotation relative to said one connecting members an to each other after being rotated relative to each other into a distinct relative angular position; and means for fixing said rings of the other of said connecting members against rotation relative to said other connecting member and to each other after being rotated relative to each other into a relative angular position corresponding to said distinct relative angular position.

11. A connector as defined in claim 10, wherein said connecting members have a housing with a positioning means for positioning said connecting members for alignment with each other.

12. A connector as defined in claim 10; and further comprising:

means for sealing said flow path and including a sealing ring mounted on one of said two elongated communication tubes.

13. A connector as defined in claim 10, wherein each of said members has a plurality of two of said rings spaced radially apart from each other and being radially inside of said releasably keeping means, said projections being formed and arranged relative to each other and to said releasably keeping means so as to have at most one relative angular position in which said connecting members are releasably kept together out of a total of 72×72×72 different possible combinations of said relative angular positions.

14. A connector as defined in claim 10, wherein said releasably keeping means includes a plurality of two hook connecting means and two receiving means formed on said connecting members, said two hook connecting means being formed with different widths, said two receiving means being formed with corresponding widths so that said two hook connecting means is fittable on said two receiving means.

* * * * *